United States Patent [19]
Aasjord et al.

[11] Patent Number: 5,804,199
[45] Date of Patent: Sep. 8, 1998

[54] OIL-BASED AND WATER-BASED ADJUVANT MIXTURE

[75] Inventors: Per Martin Aasjord, Flaktveit; Audun Helge Nerland, Skjoldtun; Dag Harald Knappskog, Sandviken, all of Norway

[73] Assignee: Akzo Nobel N. V., Arnhem, Netherlands

[21] Appl. No.: 681,130

[22] Filed: Jul. 22, 1996

Related U.S. Application Data

[63] Continuation of Ser. No. 278,431, Jul. 21, 1994, abandoned.

[30] Foreign Application Priority Data

Jul. 26, 1993 [EP] European Pat. Off. .............. 93202206

[51] Int. Cl.$^6$ ........................ A61K 39/106; A61K 9/127; A61K 39/335; A61K 31/715
[52] U.S. Cl. .................. 424/261.1; 424/423; 424/184.1; 424/450; 424/812; 424/827; 424/234.1; 424/252.1; 514/54
[58] Field of Search .............................. 424/184.1, 261.1, 424/450, 812, 423, 827, 234.1, 252.1; 514/54

[56] References Cited

U.S. PATENT DOCUMENTS

| | | | |
|---|---|---|---|
| 3,862,313 | 1/1975 | Fryer et al. ................................ | 424/92 |
| 3,943,247 | 3/1976 | Komatsu et al. ........................ | 424/180 |
| 4,223,014 | 9/1980 | Garrison et al. . | |
| 4,287,179 | 9/1981 | Amend . | |
| 4,333,922 | 6/1982 | Herschler . | |
| 4,705,780 | 11/1987 | Massot et al. . | |
| 4,769,363 | 9/1988 | Misaki et al. .............................. | 514/54 |
| 4,845,042 | 7/1989 | Newman et al. . | |
| 4,938,956 | 7/1990 | Howard et al. . | |
| 4,962,094 | 10/1990 | Jamas et al. . | |
| 4,965,347 | 10/1990 | Misaki et al. ............................. | 536/1.1 |
| 5,032,401 | 7/1991 | Jamas et al. . | |
| 5,057,503 | 10/1991 | Czop et al. . | |
| 5,109,025 | 4/1992 | Hoskinson et al. . | |
| 5,147,862 | 9/1992 | Nikl et al. ................................. | 514/54 |
| 5,165,925 | 11/1992 | Leong . | |
| 5,189,028 | 2/1993 | Nikl et al. ................................. | 514/54 |
| 5,284,653 | 2/1994 | Wolf-Watz et al. . | |
| 5,376,369 | 12/1994 | Allison et al. . | |
| 5,401,727 | 3/1995 | Rorstad et al. . | |
| 5,409,698 | 4/1995 | Anderson et al. . | |
| 5,488,040 | 1/1996 | Jamas et al. . | |
| 5,498,414 | 3/1996 | Thornton et al. . | |
| 5,504,079 | 4/1996 | Jamas et al. . | |
| 5,536,658 | 7/1996 | Shotts et al. . | |

FOREIGN PATENT DOCUMENTS

| | | | |
|---|---|---|---|
| 1310922 | 12/1992 | Canada . | |
| 2128742 | 1/1995 | Canada . | |
| 1335663 | 5/1995 | Canada . | |
| 1108575 | 9/1995 | China . | |
| 0384323 | 8/1990 | European Pat. Off. | ....... A61K 39/39 |
| 0466037 | 1/1992 | European Pat. Off. . | |
| 0640348 | 3/1995 | European Pat. Off. . | |
| 2509177 | 1/1983 | France . | |
| 3834729 | 4/1990 | Germany . | |
| 2256620 | 10/1990 | Japan . | |
| 92/06599 | 4/1992 | WIPO | .............................. A23K 1/00 |
| 9206599 | 4/1992 | WIPO . | |
| 9300160 | 1/1993 | WIPO . | |
| 9407995 | 4/1994 | WIPO . | |
| 9611707 | 4/1996 | WIPO . | |

OTHER PUBLICATIONS

Enders et al. 1990. In: Vaccines 90. Modern Approaches to New Vaccines Including Preventing Aids. Eds. Fred Brown et al. pp. 29–45.
Chen et al, 1992, J. Fish Disease, 15 : 295–304.
Reynolds et al, 1980, Inf & Imm. 30 (1): 51–57.
Hilgers et al, 1986, Int. Archs Allerg. Appl. Immun. 79: 392–396.
Teerlink et al, 1987, Vaccine, 5: 307–314.
Hilgers et al, 1992, Res Immunol, 143: 494–503.
Jørgensen et al, 1993, J Fish Diseases, 16: 313–325.
Jørgensen et al, 1993, J. Fish Diseases, 3: 267–277.
de Baulny et al, 1996, Dis. Aquatic Organisms 26: 139–147.
Jeny et al, 1993, Aquaculture 116:315–329.
Hastings et al, 1990, J. Aquatic Animal Health, 2:135–140.
Brattgjerd et al, 1994, Immumology, 83:288–294.
Meira et al, 1996, Am. J. Trop. Med. Hyg 55(5):496–503.
Engstad et al, 1995, J. Mar. Biotechnol., 3:203–207.
Jørgensen et al, 1995, Dev.& Comp. Immunol., 19(1):43–57.
Synder et al, 1980. J. Reticuloendothelial Soc., 28(1):49–54.
Benda et al, 1992, Berl. Münch Tierarzl. Wschr. 105: 95–96.
Cook et al., 1983, Immunogenicity of soluble and particulate antigens from *Leishmania donovani* : Effect of glucan as an adjuvant, Infection & Immunity, 40(3):1038–1043.
Reynolds et al., 1980, Glucan–induced enhancement of host resistance to selected infectious diseases, Infection & Immunity, 30(1):51–57.
Sharma et al., 1984, Immunization of guinea pigs against *Entamoeba Histolytica* using glucan as an adjuvant, Int. J. Immunopharm. 6(5):483–491.

*Primary Examiner*—Nita Minnifield
*Attorney, Agent, or Firm*—Sharon N. Klesner; Mary E. Gormley

[57] ABSTRACT

The invention relates to a vaccine comprising an antigenic substance and a mixture of two adjuvants wherein one adjuvant is oil-based whereas the other adjuvant is water-based.

9 Claims, 7 Drawing Sheets

OIL-BASED AND WATER-BASED ADJUVANT MIXTURE

This is a continuation of application Ser. No. 08/278,431 filed Jul. 21, 1994, now abandoned.

FIELD OF THE INVENTION

The present invention is concerned with a vaccine comprising an antigenic substance and an adjuvant, a method for the preparation of such a vaccine and an adjuvant composition.

BACKGROUND OF THE INVENTION

Most diseases in aquaculture are caused by opportunistic pathogens, i.e. bacteria which cause disease when the fish or shrimp are weakened or stressed. This is a situation which often exists under practical farming conditions.

Bacteria which are threat to commercial aquaculture are for example, *Yersina ruckeri*, the causal agent of enteric redmouth disease; *Vibrio anguillarum*, the causal agent of classical *vibriosis; Vibrio salmonicida* which causes cold water *vibriosis, Aeromonas salmonicida* which causes *furunculosis*, and *Renibacterium Salmoniarum* the causative agent of bacterial kidney disease.

The use of vaccines and antibiotics are the two available methods to protect farmed fish against diseases. The use of antibiotics has to be considerably reduced in aquaculture to avoid enviromental hazards and the risk of the development of antibiotic resistence.

For some bacterial fish pathogens the use of (experimental) vaccines have been reported (Holm, K. O. et al., J. Fish Diseases 11, 389–396, 1987; Rørstad, G. et al., Conference on Diseases in Asian Aquaculture, November 1990, Indonesia).

However, a need exists to further improve the vaccine efficacy against some of the above mentioned pathogens. Moreover, no efficient vaccine exists yet against such commercially important diseases as furunculosis and bacterial kidney disease in salmonids, and against viral diseases. For example, a threat to commercial aquaculture is represented by Aeromonas salmonicida. The vaccination against this pathogen with killed bacteria result in only poor protection, probably because of the poor immunogenicity of the antigens of the inactivated bacteria.

Therefore, with such inactivated vaccines there is a constant need for enhancing the immunogenicity of the antigens, e.g. by means of adjuvants.

Presently, there are several oil-adjuvated vaccines commercially available in Norway, two of these are tri-valent vaccines (APOJECT 3-FURAL, Apothekernes Laboratorium A.S.; BIOJEC 1900, Biomed Inc). These are tri-valent vaccines comprising inactivated whole bacteria used for the protection against *vibriosis, coldwater vibriosis* and *furunculosis* in salmon.

A disadvantage of these vaccines is their relatively poor efficacy against furunculosis and less favourable physical properties, in particular viscosity or stability of the emulsion.

A further vaccine against the said diseases which vaccine comprises a water-based adjuvant, i.e. is free of oil, is commercially available from NorBio A/S (NORVAX TRIPPEL). The water-based adjuvant in this vaccine is a β-1,3 and β-1,6 linked glucan from *S. cerevisiae* (MACROGARD, available from KS Biotec-Mackzymal, Tromsø, Norway).

A group of water-based adjuvants is represented by glucans from yeasts and mycelial fungi (DiLuzio, N. R., Springer Seminars in Immunopathology 8, 387–400, 1985). These glucans are one of the most important structural elements of fungal cell walls in general (Rosenberger, R. F., The cell wall. In: The Filamentous Fungi, Vol. 2, eds.: Smith & Berry, 328–334, 1976).

In particular, a β-1,3 and β-1,6-linked glucan from cell walls of *Saccharomyces cerevisiae* and other fungal β-glucans have been shown to enhance the resistance of fish against bacterial infection (Rørstad, G. et al., Fish & Shellfish Immunology 3, 179–190, 1993; Yano, T. et al., J. Fish Diseases 14, 577–582, 1991).

SUMMARY OF THE INVENTION

The present invention provides a vaccine comprising an antigenic substance and an adjuvant, characterized in that the adjuvant is a combination of a water-in-oil emulsion and an immunostimulating glucan.

It is known in the art that the adjuvant-effect of a water-in-oil (w/o) emulsion partly resides in its sustained release effect, i.e. the antigenic substance present in the dispersed aqueous phase is slowly released from the continuous oil phase because the oil phase gradually breaks down thereby achieving a sub-optimal stimulation of the immune system immediately after vaccination.

On the contrary, the water-based immunostimulating glucan is directly available for triggering an immune response. It could be anticipated that incorporating the water-based immunostimulating glucan into the dispersed aqueous phase of the w/o-emulsion resulted in a withdrawal of this adjuvant component from the immune system.

Surprisingly, it has been found that a vaccine comprising the adjuvant combination as defined above induced a highly protective immune response even within a short term after vaccination.

With the term immunostimulating glucan is meant a polysaccharide constituted of recurring monosaccharide units of the D-glucose type which glucan is able to increase the immune response elicited in an animal against an antigenic substance when administered in conjunction with the antigen over that immune response observed when the glucan has not been co-administered.

DETAILED DESCRIPTION OF THE INVENTION

Figure 1:
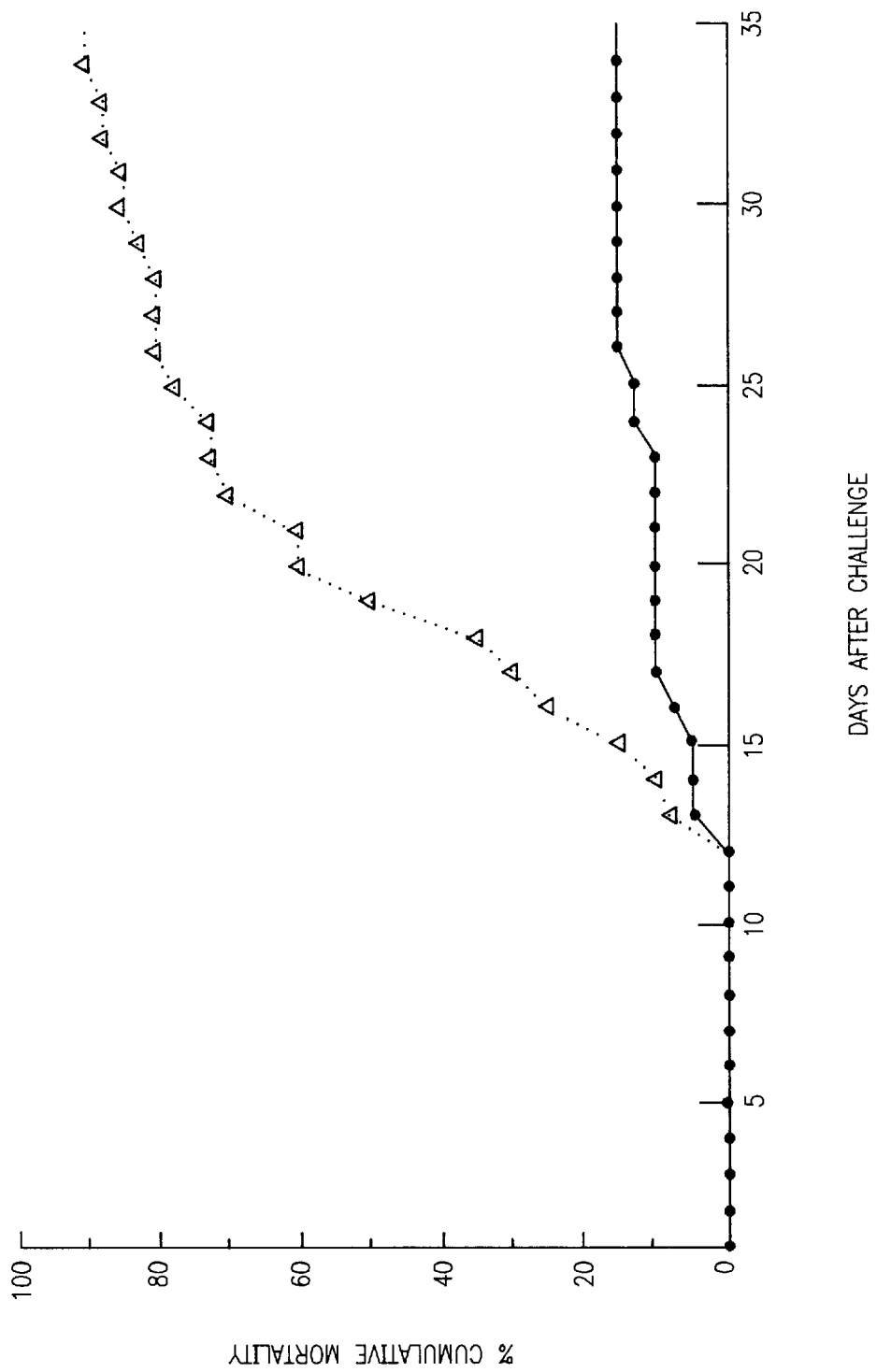

Preferably β-glucans, in particular β-glucans obtainable from fungal cell walls, are used herein as an adjuvant component. These glucans are known to be powerful stimulators of the immune system in both a non-specific and specific manner (Czop, J. K. et al., J. Immunol. 135, 3388–3393, 1985; Ross, G. D. et al., Complement 4, 61–74, 1987; DiLuzio, 1985, supra). Examples of such β-glucans are Schizofiran, scleroglucan and lentinan derived from *Schizophyllum commune, Sclerotium glucanium* and *Lentinus edodes*, respectively (Yano et al, Nippon Suisan Gakkaishi 55, 1815–1819, 1989).

In particular, preferred β-glucans are the glucans obtainable from *Saccharomyces cerevisiae* cell wall, especially a β-1,3-1,6 linked glucan (DiLuzio et al., Int. J. Cancer 24, 773–779, 1979; Rørstad, G. et al., 1993 supra), e.g. M-Glucan (MACROGARD adjuvant, obtainable from KS Biotec-Mackzymal, Tromsø, Norway).

The amount of glucan in the vaccine according to the invention is dependent from both the type of glucan chosen, the w/o-emulsion and the specific antigen in the vaccine, but preferably varies between about 1 and 1000 μg per dose and in particular between about 50 and 600 μg per dose. It is most preferred to use about 300 μg per dose.

The individual components of the w/o-emulsion to be used in the present invention are conventional and well known to the person skilled in the art.

The oil component includes mineral oils such as BAYOL (R) and DRAKEOL(both liquid parafin oils), however metalbolizable, nontoxic oils, preferably one of 6 to 30 carbon atoms including, but not limited to, alkanes, alkenes, alkynes, and their corresponding acids and alcohols, the ethers and esters thereof, and mixtures thereof. The oil may be any vegetable oil, fish oil, animal oil or synthetically prepared oil which can be metabolized by the body of the subject to which the adjuvant will be administered and which is not toxic to the subject. The subject is an animal, typically a mammal, bird or fish.

Any metabolizable oil, particularly from an animal, a fish or a vegetable source may be used herein.

Sources for vegetable oils include nuts, seeds and grains. Peanut oil, soybean oil, coconut oil, and olive oil, the most commonly available, exemplify the nut oils. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene. Squalane, the saturated analog to squalene, is also a preferred oil. Fish oils, including squalene and squalane, are readily available from commercial sources or may be obtained by methods known in the art.

The oil component of these vaccine formulations will be present in an amount from 40 to 90% by weight, especially in an amount of 60 to 80% (w/w). It is most preferred to use about 70% oil (w/w).

As is well known, the formation of a water-in-oil emulsion involves suitable choice of emulsifying agents, having regard to the relative proportions of the oil and water phases and their exact nature. Variations of the proportions of the emulsifying agent(s) is permissible but preferably should be chosen as to type and used in respective concentrations to give a final hydrophilic-lipophilic balance (HLB) number below 6.

Exemplary emulsifying agents useful in carrying out the concept of this invention include SPAN 80, SPAN 85, ARLACEL 85 and ARLACEL 83 (polyoxyethylene sorbitan mono-, di, or triester non-ionic detergents).

In particular suited for the preparation of a w/o-emulsion to be incorporated into a vaccine according to the invention are the oil-emulsifying agent combinations described in PCT-patent application WO 91/00107 comprising a metabolizable oil and an emulsifying agent of the manning monooleate family.

In the vaccine according to the invention the adjuvant combination is mixed with an antigen. The word antigen refers to any substance, including whole viruses or bacteria (live or inactivated), isolated parts or extracts thereof, or subunits (e.g. produced by recombinant technics) such as a purified protein, protein-polysaccharide, protein-lipopolysaccharide, lipo-polysaccharide, and the like, when foreign to the bloodstream of an animal stimulates the formation of specific mediators of the immune system such as B-cells, T-cells or macrophages.

Antigens may be produced by methods known in the art or may be purchased from commercial sources.

The formulation of a vaccine of the invention will employ an effective amount of an antigen, i.e. an amount of antigen which will cause the vaccinated animal to produce a specific and sufficient immunological response so as to impart protection against subsequent exposure to the pathogen immunized against. The required effective amount of antigen is dependent on the type of pathogen immunized against which protection is sought and the type of antigen used. The determination of this amount lies within the purview of the person skilled in the art.

The antigens can be, for example: viruses, bacteria or parasites. If desired, these pathogens can be killed by chemical or by physical means. In this context killing signifies inactivation, for example by such a change in the genetic material and/or other vital components that the pathogen immunized against is no longer capable of reproduction. Suitable chemical agents for killing pathogens are, for example, formaldehyde, glutaraldehyde, β-propiolactone, ethyleneimine and derivatives, or another compound which can react bifunctionally or multifunctionally with reactive groups belonging to the pathogens. Physical agents for killing pathogens are, for example, UV radiation, γ-radiation, "heat shock" and X-radiation.

Vaccines of the invention may be used to immunize birds, mammals and fish against disease causing pathogens, including without limitation *Vibrio anguillarum, Vibrio salmonicida, Aceromonas salmonicida, Renibacterium salmoninarum, Yersinia nuclerii* and genetically modified fish pathogens, Infectious Bronchitis virus, Newcastle Disease virus, Gumboro Disease virus, Pseudorabies virus, *Actinobacillus pleuropneumoniae* and *E. coli*.

In particular, the vaccine according to the invention is suited for immunizing fish against one or more pathogens such as *Aeromonas salmonicida, Vibrio salmonicida, Vibrio anguillarum* and *Yersina ruckerii*.

The vaccine emulsion described above may be produced by methods known in the art for this purpose such as described inter alia in Herbert, W. J., in: Handbook of Experimental Immunology Vol. 3, ed.: D. M. Weir, 3th edition, 1979; Pharmaceutical Dosage Forms Vol. 1, eds.: Lieberman, H. A., Rieger, M. M. and Banker, G. S., 199–284, 1988.

For example the oil phase containing the emulsifying agent is mixed slowly with the aqueous antigenic phase further containing the glucan under agitation by for example Silverson L2R agitator or Ultra Turrax T25. Alternatively, the oil, emulsifying agent and water-based glucan may be emulsified first and subsequently mixed with the aqueous antigen phase.

EXAMPLE 1

Vaccine preparation

NORVAX TRIPPEL (Commercially available from Nor-Bio A/S, Bergen, Norway), a whole bacterial cell vaccine comprising MACROGRAD glucan as an adjuvant, and further containing formalin inactivated *Vibrio anguillarum* O1, *Vibrio anguillarum* O2, *Vibrio salmonicida* and *Aero-* monas salmonicida, var. salm is mixed with Montanide (R) ISA 715 (available from Seppic, Pharma Division, Paris, France) an oil composition comprising an oil and an emulsifying agent from the manning monooleate family in a ratio of 30/70 (w/w) and emulsified using an Ultra Turrax.
Vaccination trial Standard test conditions: Fish size: 15–20 g. (Atlantic salmon—Salmo salar L) Tank size: 150 litres (0.6×0.6 m). Water temperature: 11° C. Starvation: 2 days prior to treatment. Feeding starts 12 hours after handling Anaesthetizing procedure prior to vaccination or challenge: 1 ml 30% chlorbutanol per. litre water is used. The vaccination takes place as soon as the fishes are anaesthetized. The fishes are recovered by flushing in water. Reisolation of bacteria: Aeromonas salmonicida var. salm. is reisolated from the kidney by plating on blood agar dishes and incubated at 15°–18° C. for 3 days. Colonies are microscopically examined for indentification of the bacteria on the basis of morphology.
Vaccines: NORVAX TRIPPEL with adjuvant mixture (described above). APOJECT 3-FURAL (Apothekernes Laboratorium A/S) containing an oil-based adjuvant and the same antigens as NORVAX TRIPPEL. BIOJEC 1900 (Biomed Inc.) containing an oil-based adjuvant and the same antigens as NORVAX TRIPPEL.
Vaccination procedure:
40 fishes were intraperitoneally injected with 0.2 ml of ISA 715 emulsified NORVAX TRIPPEL. 40 fatfin tagged fishes injected 0.2 ml 1.2% NaCl served as controls. The same procedure was used for APOJECT 3-FURAL and BIOJEC 1900.
Challenge procedure:
The challenges took place 11, 22 and 27 weeks after vaccination. The vaccinated and the control groups were both infected in the same tank. The challenge was performed by injection of Aeromonas salmonicida var. salm. using the following cohabitation method: $2 \times 10^4$ bacteria in 0.1 ml were intraperitoneally injected into each of 5 fishes, which then are put into each tank containing both vaccinated and control fishes. The cohabitants normally die within 5–8 days. The fishes were observed over a period of 35 days and the mortality recorded. The challenge is terminated and the RPS (Relative Percentage Survival) is calculated after 5 days without mortality.
Calculation of Relative Percentage Survival (RPS):

$$\% RPS = 100\% \left(1 - \frac{\% \text{ loss vaccinated fish}}{\% \text{ loss control fish}}\right)$$

Figure 2:
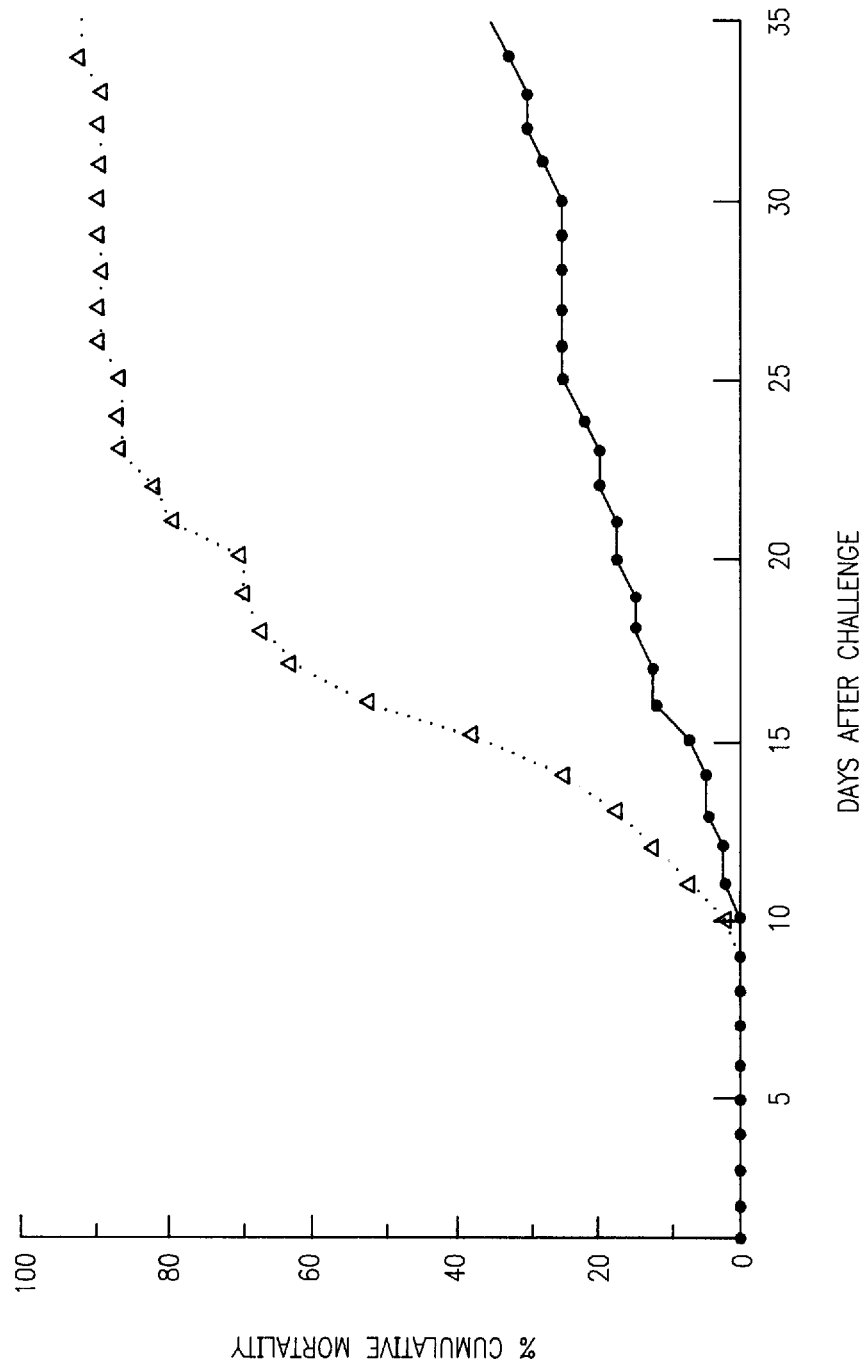
Figure 3:
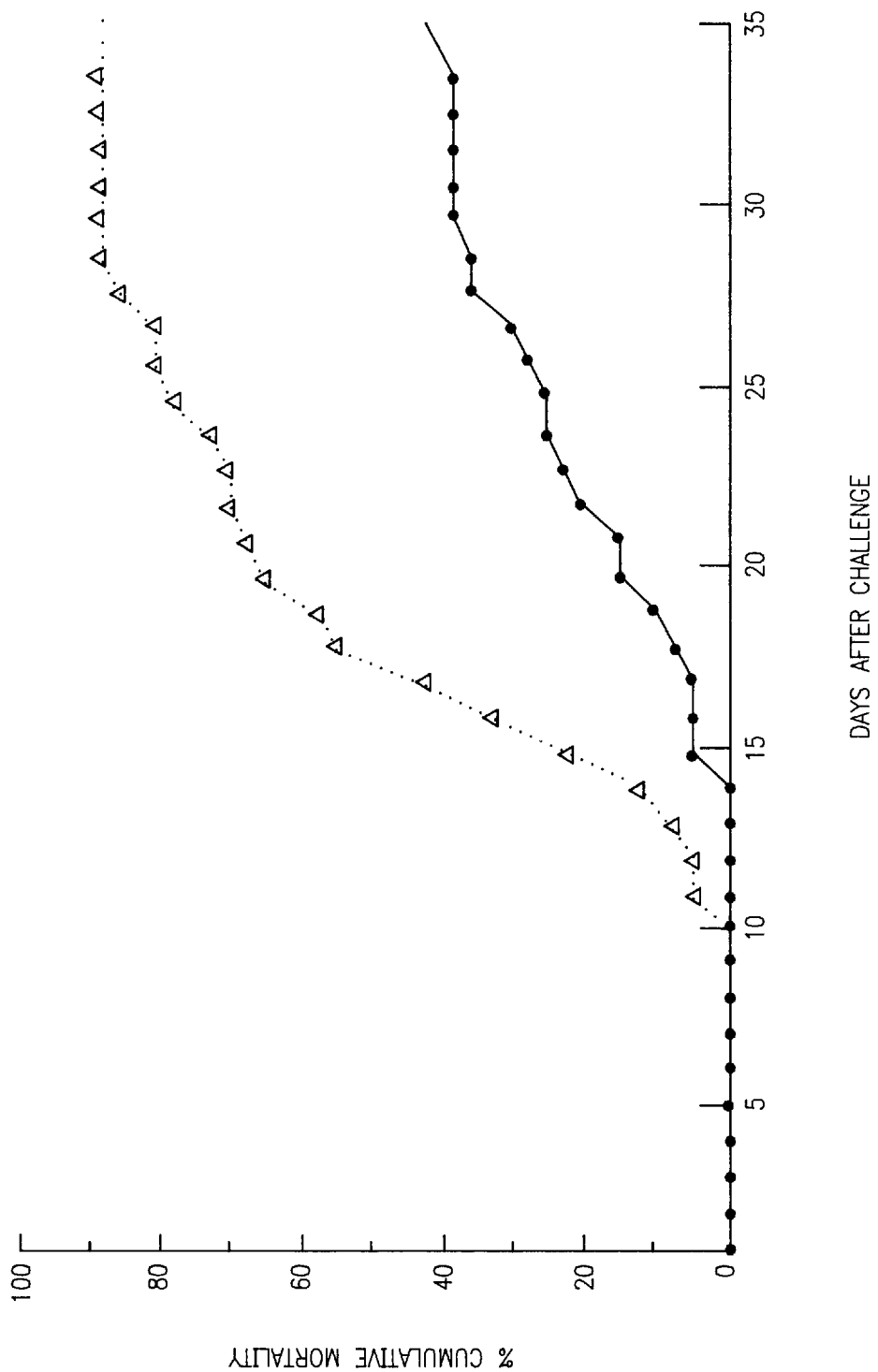
Figure 4:
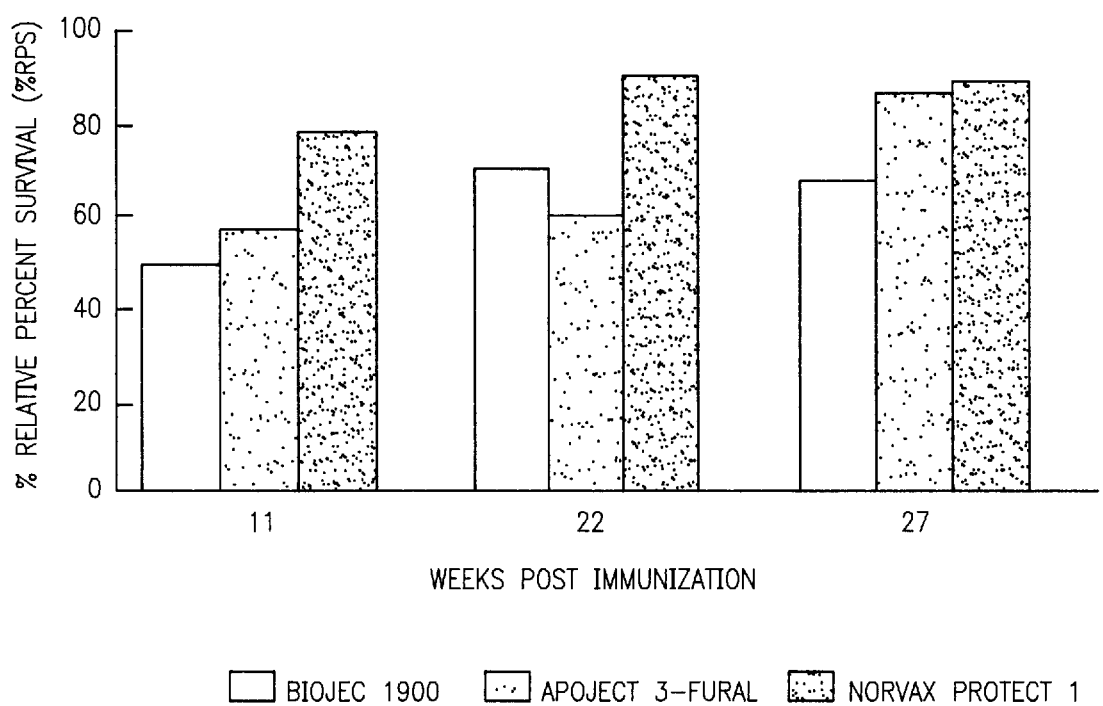

Results:
A vaccine demonstrates a sufficient protective capacity if the RPS for Aeromonas salmonicide var. salm. is at least 60%. The mortality profile for NORVAX TRIPPEL ISA 715, APOJECT 3-FURAL and BIOJEC 1900 after the first challenge are shown in FIGS. 1–3, respectively. The RPS values were calculated to be 83,5%, 62,2% and 54,3%, respectively. In FIG. 4 these RPS values are shown in a diagram and the RPS-values for the challenge after 22 and 27 weeks is added. At all moments the Norvax Trippel ISA 715 gives the highest survival.

EXAMPLE 2

Vaccine preparation
Four test vaccines were produced, composed of different combinations of antigens, glucan and oil:
(1) Antigens
(2) Antigens+glucan
(3) Antigens+oil,
(4) Antigens+glucan/oil.

The antigens used are the same as in Example 1. As glucan a b-1,-3 glucan extracted from the cell wall of the yeast fungus Saccharomyces cerevisia (Biotech Makzymal) was used and as oil Montanide ISA 715 (Seppic) was used. The vaccines were prepared in the same way as described under Example 1.
Housing
During the first period the experimental fishes (pre-smolt Atlantic salmon (Salmo salar L.)) were finn-clipped and kept in separate indoor tanks (0.6 $m^3$). In order to copy a natural production cycle, the fishes were gradually adapted to sea water condition during the smoltification period (May-July). In October all groups were transferred to a large outdoor tank (20 $m^3$). The fishes were tagged in order to recognize the different experimental groups. The fishes were fed a commercial dry feed in surplus. Food was dispensed from automatic feeders. The fishes were kept under seasonally changing water temperatures and light condition.
Vaccination procedure
Vaccination was performed using standard conditions (see Example 1).
Challenge procedure
Groups of 30 fishes of each vaccinated group were challenged at 18 and 31 weeks post vaccination. To each experimental group an equal number of control fishes were added. The challenges were performed in four different tanks, each housing one experimental and one control group.
The fishes were infected with Aeromonas salmonicida var. salm. by cohabitation. Mortality was recorded daily during a period of 30–45 days post challenge. The challenge trials were ended after five days without mortality and the RPS was calculated.
Immunological assay
Blood samples were collected 0, 4, 8, 18, 31, 54 and 61 weeks after vaccination. The fishes were starved and anaesthetized before being bled from the caudal vein. Blood samples were coagulated at 4° C. for 12–24 hours, centrifuged at 1000 g for 5 min. and the serum fractions collected and stored in aliquots at −80° C.
Presence of specific antibodies to Aeromonas salmonicida var. salm antigen was detected by use of ELISA techniques according to standard operation procedures. Briefly, antigens were diluted in carbonate/bicarbonate buffer to a final concentration of $3.10^8$ bacteria/ml, and used for coating 96-well immunoplates (Nunc Maxi Sorb). Incubation of salmon sera (diluted 1:50–1:51400) was 18 hours at 15° C., for rabbit anti-salmon Ig (ø451, 1:6000), 1 hour at 20° C. and for goat anti-rabbit Ig (Bio-Rad) (1:3000) 1 hour at 20° C. Finally o-phenylenediamine dihydrochloride (Sigma) was added as substrate. Antibody binding was measured spectrophotometrically at 492 nm.

RESULTS

Figure 5:
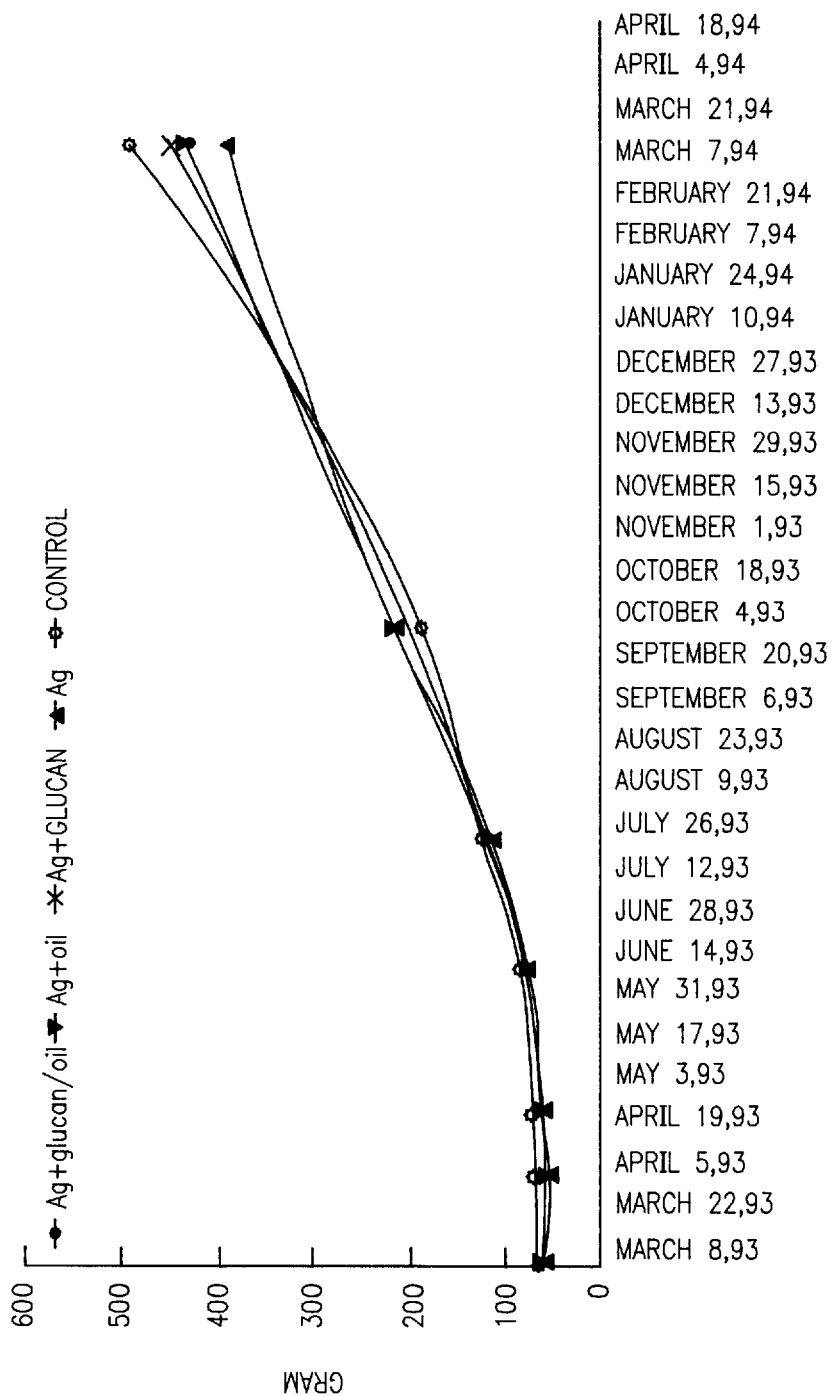
Figure 6A:
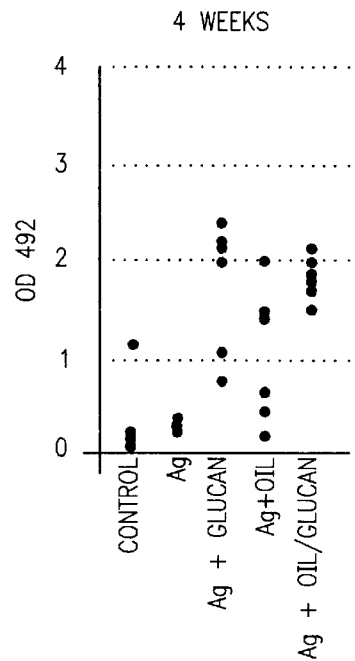
Figure 6B:
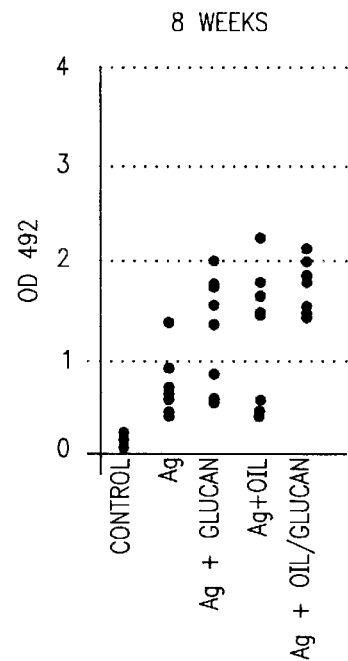
Figure 6C:
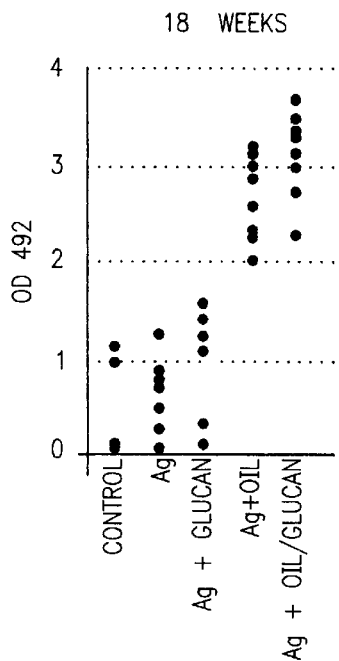
Figure 6D:
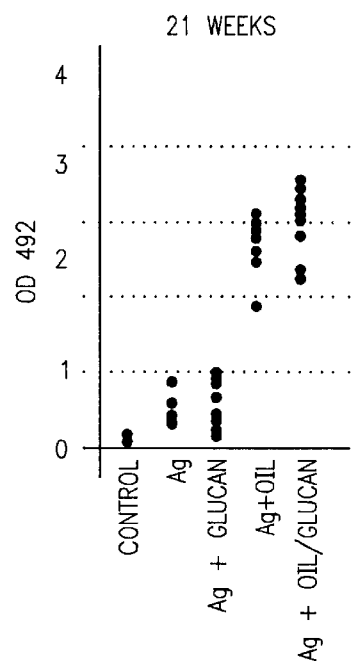
Figure 6E:
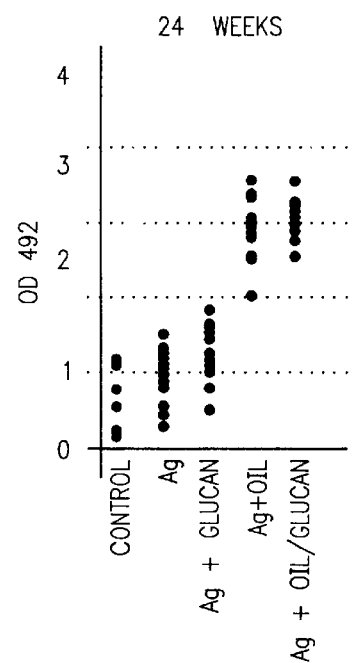
Figure 6F:
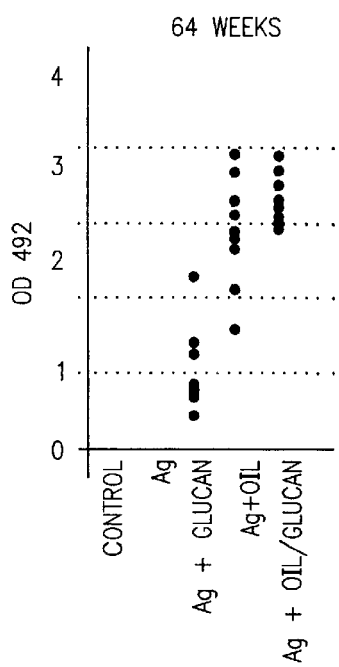
Figure 7A:
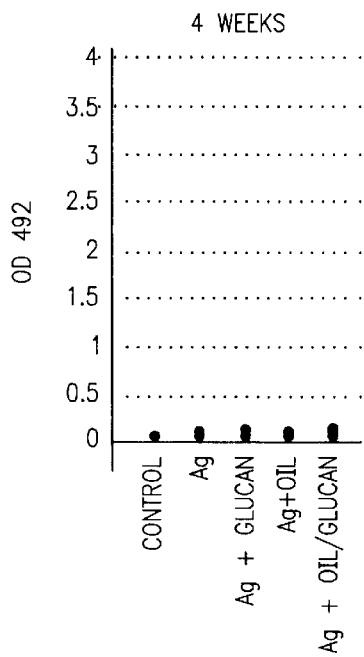
Figure 7B:
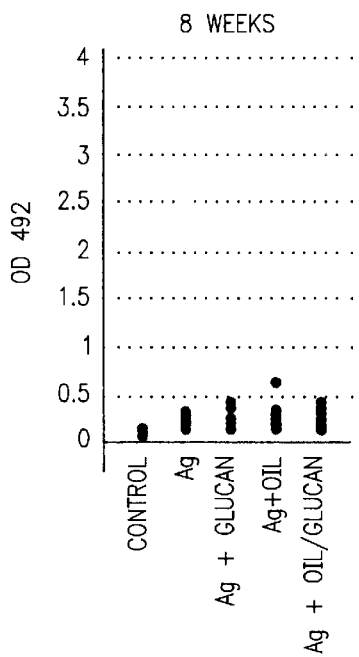
Figure 7C:
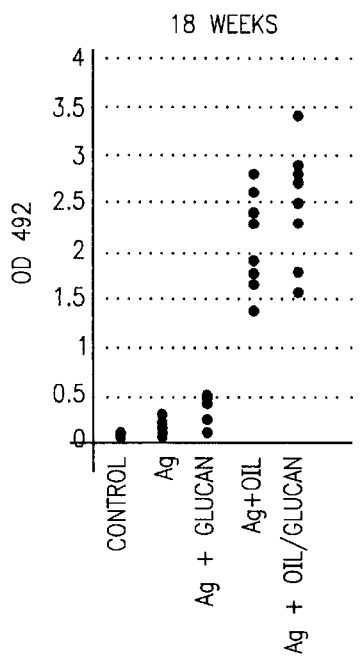
Figure 7D:
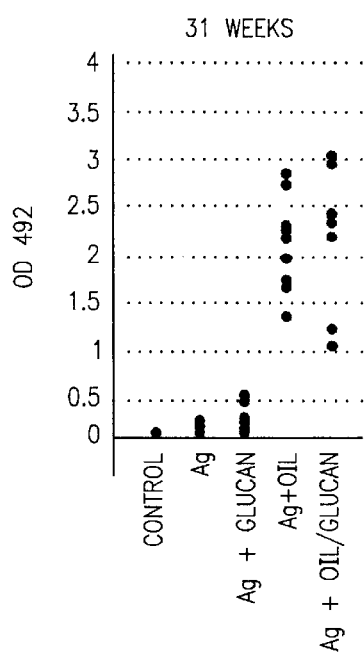
Figure 7E:
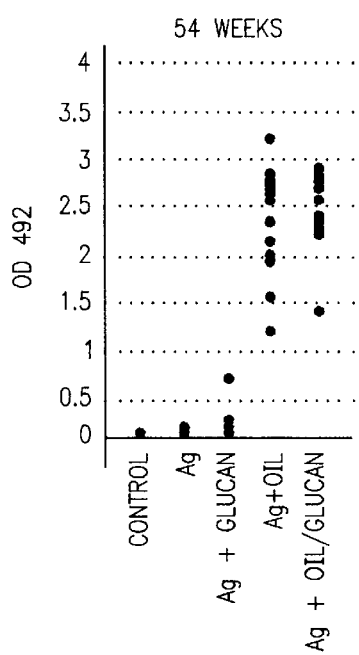
Figure 7F:
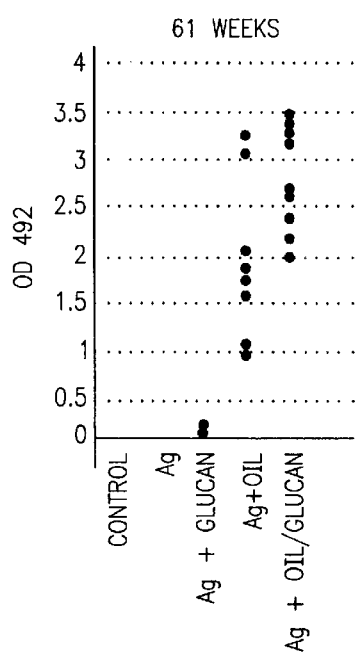

Growth and mortality
Growth during rearing in indoor tanks was similar in all experimental groups (see FIG. 5). After transfer to outdoor tanks differences in growth rate were observed, which are probably due to unequal handling of the groups. All vaccinated groups were tagged, while the control group remained untagged.
Overall mortality during the trial was invariably low in all experimental groups.
Antibody response to Aeromonas salmonicida
Serum samples from vaccinate d groups and control groups were analysed by ELISA. Titration curves for antibodies in the serum samples from the different experiments at different times post vaccination are shown in FIGS. 6 and 7. The 1:400 dilution distinguishes best the values during the first 18 weeks, while in the period from week 18 to week 61 the antibody level in the groups vaccinated with oil based vaccine reaches such high responses that for comparison a 1:3200 dilution was chosen.

Protection

The results from the challenge trials are presented in Table I. In the second trial the weight of the fish had reached approximately 200 gram. For fishes with such weight it has been found that the cohabitation challenge model is not reliable. Although the number of cohabitants was doubled, a low mortality was reached in the control group. In order to calculate relative percent survival, a minimum of 60% mortality in the control group is needed.

From the experiment it can be concluded that the double adjuvanted vaccine is characterized by a rapid onset of antibody response, which is kept on a high level throughout the experimental period. During the experimental period, the single oil vaccine never reached the same level of antibody titre as the double adjuvanted vaccine. No difference in growth rates have been observed.

The protection against infection seems to be related to the antibody titre.

Legend to the Figures:

FIG. 1–3: Challenge of Norvax Trippel ISA 715 (1), Apoject 3-fural (2) and Biojec 1900 (3) 11 weeks after vaccination.

Vaccinated fish (---•---). Control fish (--- ---).

FIG. 4: Relative Percentage Survival 11, 22 and 27 weeks after survival.

FIG. 5: Mean weights in the different experimental groups.

FIG. 6: Individual immune sera in each experimental group tested 1:400 in ELISA.

FIG. 7: Individual immune sera in each experimental group tested 1:3200 in ELISA.

TABLE 1

Cumulative mortalities and estimated RPS for the different experimental groups, in two challenge tests at two different time intervals after vaccination. The challenges were performed by cohabitation.

| Weeks after vaccination | Vaccination group | No. of deaths/ total no. of fish | % cumulative mortality | Relative percent survival |
|---|---|---|---|---|
| 18 weeks | Ag | 16/25 | 64 | 0 |
|  | Ag + glucan | 11/25 | 44 | 27 |

TABLE 1-continued

Cumulative mortalities and estimated RPS for the different experimental groups, in two challenge tests at two different time intervals after vaccination. The challenges were performed by cohabitation.

| Weeks after vaccination | Vaccination group | No. of deaths/ total no. of fish | % cumulative mortality | Relative percent survival |
|---|---|---|---|---|
|  | Ag + oil | 1/25 | 4 | 93 |
|  | Ag + oil/glucan | 0/25 | 0 | 100 |
|  | Control | 15/25 | 60 | — |
| 31 weeks | Ag | 2/25 | 8 | — |
|  | Ag + glucan | 0/25 | 0 | — |
|  | Ag + oil | 0/25 | 0 | — |
|  | Ag + oil/glucan | 0/25 | 0 | — |
|  | Control | 4/25 | 16 | — |

We claim:

1. A vaccine comprising an antigenic substance and an adjuvant comprising a combination of a water-in-oil emulsion and an immunostimulatory glucan.

2. The vaccine according to claim 1, wherein the glucan is β-glucan.

3. The vaccine according to claim 1, wherein the glucan is a β1,3-and β-1,6-linked glucan from cell walls of *Saccharomyces cervisiae*.

4. The vaccine according to claim 1, wherein the oil is selected from groups consisting of an animal oil, a vegetable oil and a synthetic oil.

5. The vaccine according to claim 1, wherein the ratio of water to oil in the emulsion is about 30/70 (w/w).

6. The vaccine according to claim 1, wherein the antigenic substance is derived from a fish pathogen.

7. The vaccine according to claim 6, wherein the fish pathogen is selected from the group consisting of *Vibrio salmonicida, Aeromas salmonicida, Renibacterium salmoninarum* and *Yersina ruckerii*.

8. An adjuvant composition comprising a water-in-oil emulsion and an immunostimulatory glucan.

9. A method for the preparation of a vaccine comprising an antigenic substance and an adjuvant, comprising emulsifying the antigenic substance and an immunostimulating glucan with an oil in the presence of an emulsifying agent such that a water-in-oil emulsion is obtained.

* * * * *